(12) United States Patent
Egeler et al.

(10) Patent No.: US 9,261,454 B2
(45) Date of Patent: Feb. 16, 2016

(54) CELL CULTURE VESSELS FOR MENISCUS REDUCTION WITH AQUEOUS SOLUTIONS

(71) Applicant: STEMCELL TECHNOLOGIES INC, Vancouver (CA)

(72) Inventors: Oliver Egeler, North Vancouver (CA); Steven M. Woodside, Calgary (CA)

(73) Assignee: STEMCELL TECHNOLOGIES INC., Vancouver (CA)

( * ) Notice: Subject to any disclaimer, the term of this patent is extended or adjusted under 35 U.S.C. 154(b) by 0 days.

(21) Appl. No.: 14/101,892

(22) Filed: Dec. 10, 2013

(65) Prior Publication Data

US 2014/0168764 A1    Jun. 19, 2014

Related U.S. Application Data

(62) Division of application No. 12/559,142, filed on Sep. 14, 2009, now Pat. No. 8,703,072.

(60) Provisional application No. 61/096,338, filed on Sep. 12, 2008.

(51) Int. Cl.
*B01L 3/00* (2006.01)
*G01N 21/03* (2006.01)

(52) U.S. Cl.
CPC .............. *G01N 21/03* (2013.01); *B01L 3/5082* (2013.01); *B01L 2300/0858* (2013.01); *B01L 2300/165* (2013.01); *B01L 2400/086* (2013.01); *B01L 2400/088* (2013.01)

(58) Field of Classification Search
CPC ................. B01L 2300/0858; B01L 2300/165; B01L 2400/086; B01L 2400/088
See application file for complete search history.

(56) References Cited

U.S. PATENT DOCUMENTS

| | | | |
|---|---|---|---|
| 4,122,980 A | * | 10/1978 | Laverty ................ A46K 5/1214 215/253 |
| 4,233,029 A | | 11/1980 | Columbus |
| 4,303,616 A | | 12/1981 | Kano et al. |
| 4,426,451 A | | 1/1984 | Columbus |
| 4,741,619 A | | 5/1988 | Humphries et al. |
| 4,831,224 A | | 5/1989 | Keefer |

(Continued)

FOREIGN PATENT DOCUMENTS

| | | |
|---|---|---|
| CA | 2216378 | 11/1996 |
| CN | 1894351 | 1/2007 |

(Continued)

OTHER PUBLICATIONS

International Preliminary Report on Patentability, issued on Aug. 26, 2009 in PCT International Application No. PCT/CA2008/000363.

(Continued)

*Primary Examiner* — Paul Hyun
(74) *Attorney, Agent, or Firm* — Bereskin & Parr LLP/S.E.N.C.R.L., s.r.l.

(57) ABSTRACT

A meniscus reducing member for use in a vessel for containing a liquid including a surface feature overlying at least a portion of an interior surface of the vessel. The surface feature includes at least two surfaces for contacting the liquid that cooperate to reduce a width of a meniscus formed at an interface between the liquid and the surface feature by physically altering a contact angle between the liquid and the surface feature.

15 Claims, 12 Drawing Sheets

(56) References Cited

U.S. PATENT DOCUMENTS

| | | |
|---|---|---|
| 5,180,555 A | 1/1993 | Monget |
| 5,540,891 A | 7/1996 | Portmann et al. |
| 6,074,614 A | 6/2000 | Hafeman et al. |
| 6,971,530 B2 | 12/2005 | Darr |
| 6,977,722 B2 | 12/2005 | Wohlstadter et al. |
| 2003/0228705 A1 | 12/2003 | Chan et al. |
| 2004/0072367 A1 | 4/2004 | Ding et al. |
| 2004/0082699 A1 | 4/2004 | Brown |
| 2005/0047971 A1 | 3/2005 | Clements et al. |
| 2005/0137355 A1 | 6/2005 | Buckanin et al. |
| 2005/0170498 A1 | 8/2005 | Dolley et al. |
| 2005/0226787 A1 | 10/2005 | Shanler |
| 2005/0244838 A1 | 11/2005 | Wojtowicz |
| 2006/0123893 A1 | 6/2006 | Johans et al. |
| 2006/0172412 A1 | 8/2006 | Perrier et al. |
| 2007/0110907 A1 | 5/2007 | Brown |
| 2007/0154357 A1 | 7/2007 | Szlosek |
| 2007/0274871 A1 | 11/2007 | Jiang |
| 2008/0072964 A1 | 3/2008 | Kim et al. |
| 2009/0217981 A1 | 9/2009 | Extrand et al. |

FOREIGN PATENT DOCUMENTS

| | | |
|---|---|---|
| EP | 1859866 | 11/2007 |
| JP | 59088084 | 5/1984 |
| JP | 2008035841 | 2/2008 |
| SU | 1455295 | 1/1989 |
| WO | 96-34697 | 11/1996 |
| WO | 03-050515 | 6/2003 |

OTHER PUBLICATIONS

Schuderer et al., "Effect of the Meniscus at the Solid/Liquid Interface on the SAR Distribution in Petri Dishes and Flasks", Bioelectromagnetics 24, 103-108, 2003.

European Patent Application No. 08714684, Supplementary European Search Report dated Nov. 22, 2013.

* cited by examiner

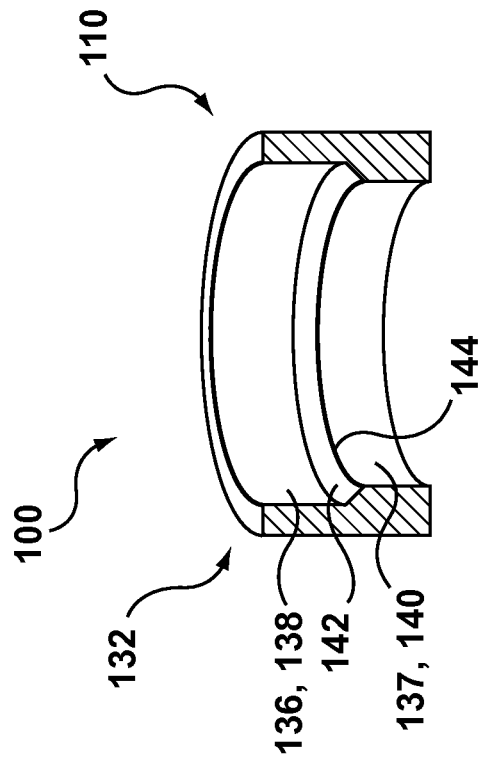
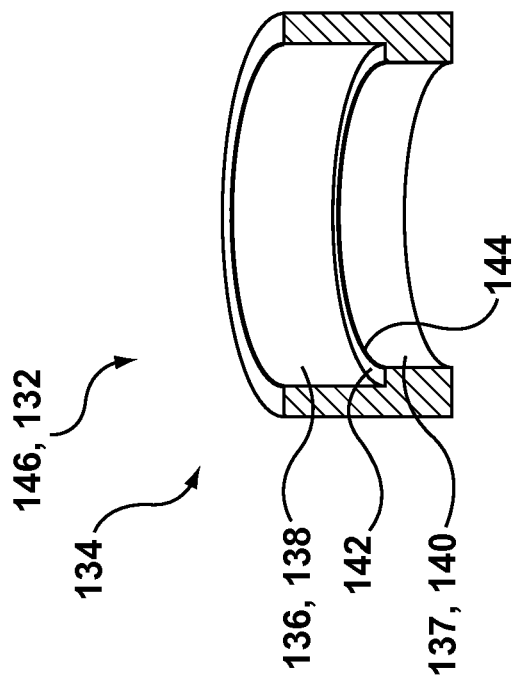

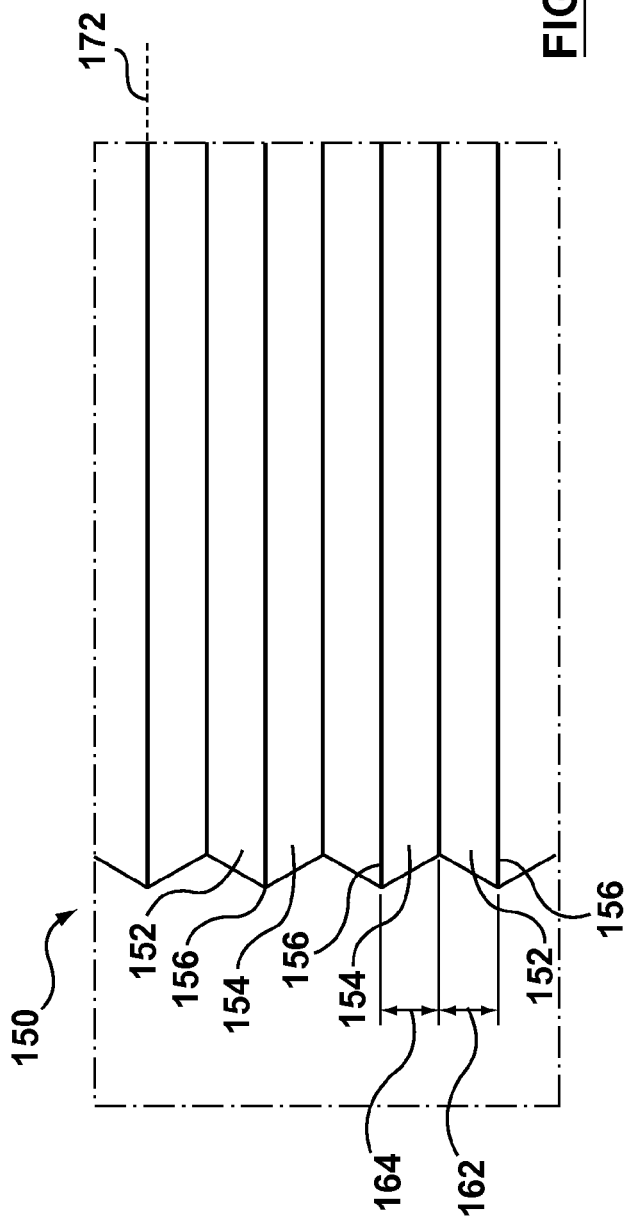

CELL CULTURE VESSELS FOR MENISCUS REDUCTION WITH AQUEOUS SOLUTIONS

CROSS REFERENCE TO RELATED APPLICATIONS

This application claims the benefit of 35 USC 119 based on the priority of U.S. patent application Ser. No. 12/559,142, filed Sep. 14, 2009 which itself is a conventional application claiming priority of U.S. provisional patent application 61/096,338, filed Sep. 12, 2008, each of those applications being incorporated herein in their entirety by reference.

FIELD

Embodiments described herein relate to vessels for holding liquid and in particular to well-plates, and in particular to well-plates configured to reduce the magnitude of the meniscus curvature when aqueous liquids are placed within the wells.

BACKGROUND

When a liquid is placed on a solid surface, the liquid surface assumes a shape that is characteristic of the physiochemical properties of the three phases involved (solid, liquid and vapor phase). The angle defined by the liquid and solid surfaces at the point of contact of the three phases is termed the "contact angle" ($\theta$). The magnitude of this angle is determined by the interfacial free energies (surface tension, $\gamma$) of the liquid-vapor (LV) interface, the liquid-solid (LS) interface, and the solid-vapor (SV) interface. In the case of liquids placed within a dish or well of a multiwell plate, a meniscus results when the contact angle between the liquid and the solid surface is other than 90 degrees. When the contact angle is less than 90 degrees, a concave meniscus is formed, and when the contact angle is greater than 90 degrees, a convex meniscus is formed.

Due to the contact angle properties defined above, surface energies of the solution and the containing solid interfaces are often cited as defining properties that determine meniscus shape and magnitude. However, physiochemical properties, in addition to surface energies of the liquid and solid surfaces, are of importance in determining meniscus shape of aqueous liquids at equilibrium. Such properties include (a) the three-dimensional topology of the solid surface, (b) the composition of the liquid phase, (c) physical and chemical heterogeneity of the solid surface, and (d) inducibility of configurational changes of the solid surface by the liquid. This causes a hysteresis in contact angles dependent on the interactions of the above mentioned surface properties, which makes the theoretical estimation of meniscus magnitude difficult based on surface chemistries. There is currently no universal theory which accurately models the contact angle in complex systems, and thus contact angle hysteresis and the resulting meniscus must be determined empirically for different liquid/solid combinations.

A meniscus presents a significant problem to any optical imaging of the objects present within a liquid containing vessel, dish or well for several reasons. The curvature of the liquid surface will cause the refraction and reflection of the illuminating light and result in optical interference within the area of the meniscus. In addition, the meniscus results in a change in liquid depth near the solid surfaces and may cause an uneven distribution of objects near the wall of the dish or well.

Several methods have been used to compensate for meniscus effects in digital microscopy. Observations can be limited to central portions of a well or the light exposure can be increased when imaging within the meniscus. Physical barriers, such as coverslips, have also been used to compress the meniscus. However, such methods are cumbersome and can reduce the sampled image area so as to omit relevant areas of cell cultures and render the method not quantitative.

One technique for mitigating meniscus formation is to compose the solid surface of the vessel wall from a polymeric material that provides surface properties at the liquid-solid interface between a particular polymeric material and a particular liquid so as to result in a dynamic minimum contact angle of approximately 90 degrees. Alternately, a polymeric coating may be applied to the wall surface to impart those same properties to the surface. However, since these surface properties of the liquid-solid interface are dependent on the complex interactions between physiochemical properties of the liquid as well as the solid surface chemical and physical heterogeneity, different wall polymers or surface coatings would be required for liquids with dissimilar properties.

A uniform method that is effective for reducing meniscus magnitude with a wide variety of aqueous solutions with various surface energies would be advantageous for many imaging and biological applications.

SUMMARY

This summary is intended to introduce the reader to the more detailed description that follows and not to limit or define any claimed or as yet unclaimed invention. One or more inventions may reside in any combination or sub-combination of the elements or process steps disclosed in any part of this document including its claims and figures.

Physical surface modifications to the interior wall surface of cell culture vessels that effect a reduced meniscus magnitude and a resultant diminished optical interference during imaging are described. The cell culture vessel can be any vessel including, without limitation, cell culture dishes or multiwell plates.

In accordance with a first aspect, some examples of a meniscus reducing member for use in a vessel for containing a liquid comprise a surface feature overlying at least a portion of an interior surface of the vessel. The surface feature includes at least two surfaces for contacting the liquid. The at least two surfaces cooperate to reduce a magnitude of a meniscus formed at an interface between the liquid and the surface feature by physically altering a contact angle between the liquid and the surface feature.

In some examples, the at least two surfaces comprise first and second inner faces, a step face extending between the first and second inner faces and a step edge defined by the intersection of the second inner face and the step face.

In some examples, the first and second inner faces are perpendicular to a lower plane of the vessel and the second inner face is inwardly offset from the first inner face.

In some examples, the step face is perpendicular to the first and second inner faces.

In some examples, the step face is inclined at an oblique angle to both the first and second inner faces.

In some examples, the step face is substantially planar.

In some examples, the at least two surfaces comprise a plurality of alternating first and second surface regions, each first surface region having a first surface energy and each second surface region having a second surface energy, the second surface energy being different than the first surface energy.

In some examples, the first surface region has a relatively lower degree of hydrophobicity than the second region.

In some examples, the first surface regions are hydrophilic and the second surface regions are hydrophobic.

In some examples, the first surface regions are hydrophobic and the second surface regions are superhydrophobic.

In some examples, the first surface regions are hydrophilic and the second surface regions are superhydrophobic.

In some examples, each of the first and second surface regions define first and second region widths respectively, each of the first and second region widths is between 0.01 and 5 mm and the first region width is equal to the second region width.

In some examples, each of the first and second surface regions define first and second region widths respectively, each of the first and second region widths is between 0.01 and 5 mm and the first region width is different than the second region width.

In some examples, the at least two surfaces comprise a corrugated member, the corrugated member comprising a plurality of pairs of converging first and second surfaces, each pair of first and second surfaces intersecting to define an edge.

In some examples, the first surface has a first slope angle and the second surface has a second slope angle, the first and second slope angles are each between 1 and 75 degrees.

In some examples, the first and second slope angles are each between 5 and 60 degrees.

In some examples, the first slope angle is different than the second slope angle.

In some examples, the first surface has a first surface width and the second surface has a second surface width, the first surface width is different than the second surface width.

In some examples, the first surface has a first surface width and the second surface has a second surface width, the first surface width is equal to the second surface width.

In some examples, adjacent edges are separated by an edge spacing distance, the edge spacing distance being set to reduce wetting of the first and second surfaces by the liquid due to a surface tension of the liquid.

In some examples, the edge spacing distance is between 0.01 and 3 mm.

In some examples, each edge has an edge height, each edge height is between 0.01 and 1.5 mm.

In some examples, the surface feature has an axis that is perpendicular to a lower plane of the vessel.

In some examples, the surface feature has an axis that is at an angle relative to a lower plane of the vessel, the angle being between 0 and 90 degrees.

In some examples, the meniscus reducing member is integral a sidewall of the vessel.

In some examples, the meniscus reducing member is disposed on a separate insert member configured to be received within the vessel.

In some examples, the surface feature extends continuously around an inner perimeter of the vessel.

In some examples, the surface feature extends around only a portion of an inner perimeter of the vessel.

BRIEF DESCRIPTION OF THE DRAWINGS

FIG. 5 is a cross-section view of an insert for a vessel including a meniscus reducing member having a flat step-like surface feature;

FIG. 6 is a cross-section view of an insert for a vessel including a meniscus reducing member having a sloped step-like surface feature;

FIG. 8 is a side view of an example of a corrugated member;

FIG. 9 is a side view of another example of a corrugated member;

DETAILED DESCRIPTION

The following description is not to be considered as limiting the scope of any claimed invention, but rather as providing an example within each claimed invention. However, each example may not be an embodiment of each claimed invention, for instance a particular claim might relate to only one exemplary device. The claims should not be interpreted as necessarily including all of the features of any example, or all of the examples or requiring features common to all of the examples. The applicants, inventors and owners reserve all rights that they may have in any invention disclosed in an apparatus or process described below that is not claimed in this document, for example the right to claim such an invention in a continuing application and do not intend to abandon, disclaim or dedicate to the public any such invention by its disclosure in this document.

An alternate approach to the chemical composition of the polymeric wall surface or coatings of the surface for the reduction of meniscus formation is presented in this application. This application relates to meniscus reducing members that reduce the magnitude of a meniscus formed within a vessel by physically interfering with meniscus formation. Examples of such a meniscus reducing member include a surface feature that is introduced onto the interior wall surface of a liquid containing vessel or well to physically interfere with meniscus formation. Examples of such surface features are explained in greater detail below.

Figure 1A:
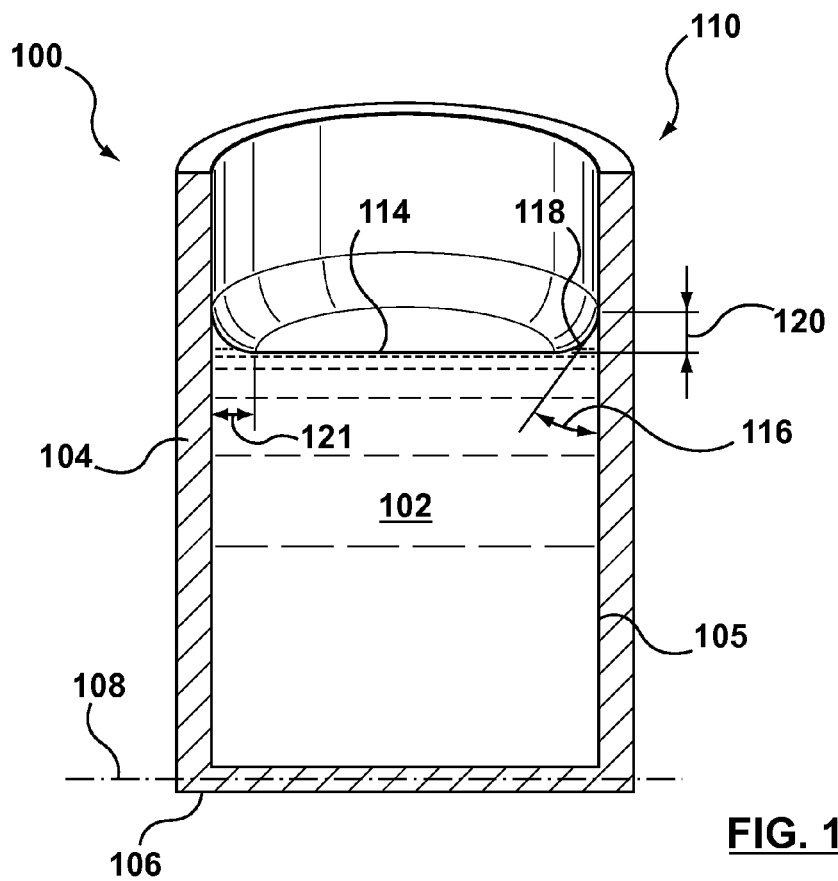
FIG. 1a is a cross-section view of a vessel containing a fluid having a contact angle less than 90 degrees.
Figure 1B:
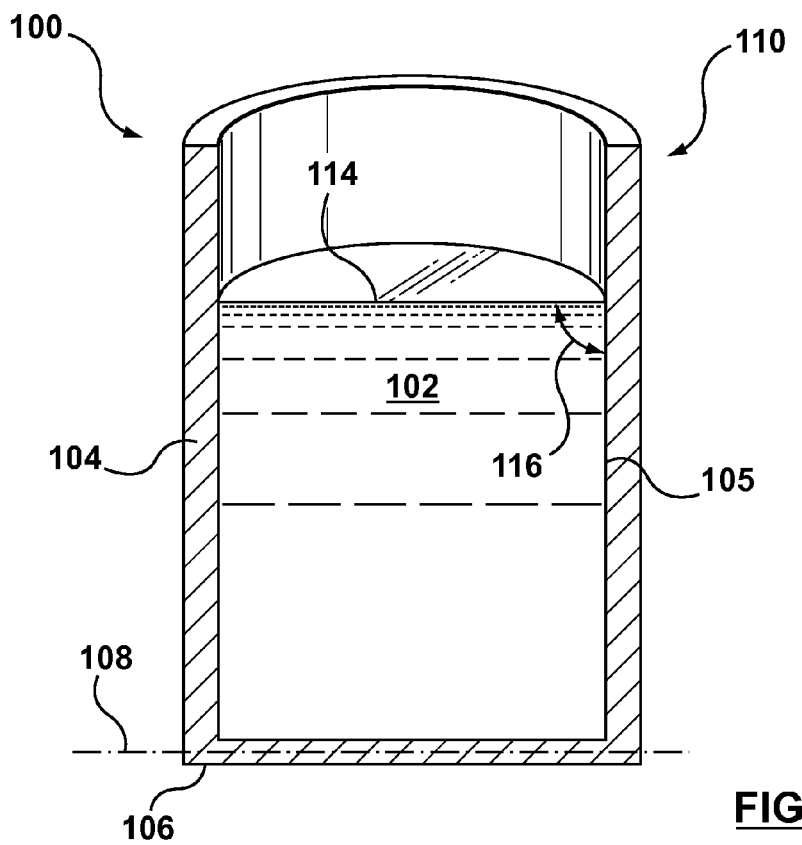
FIG. 1b is a cross-section view of a vessel containing a fluid having a contact angle equal to 90 degrees.
Figure 1C:
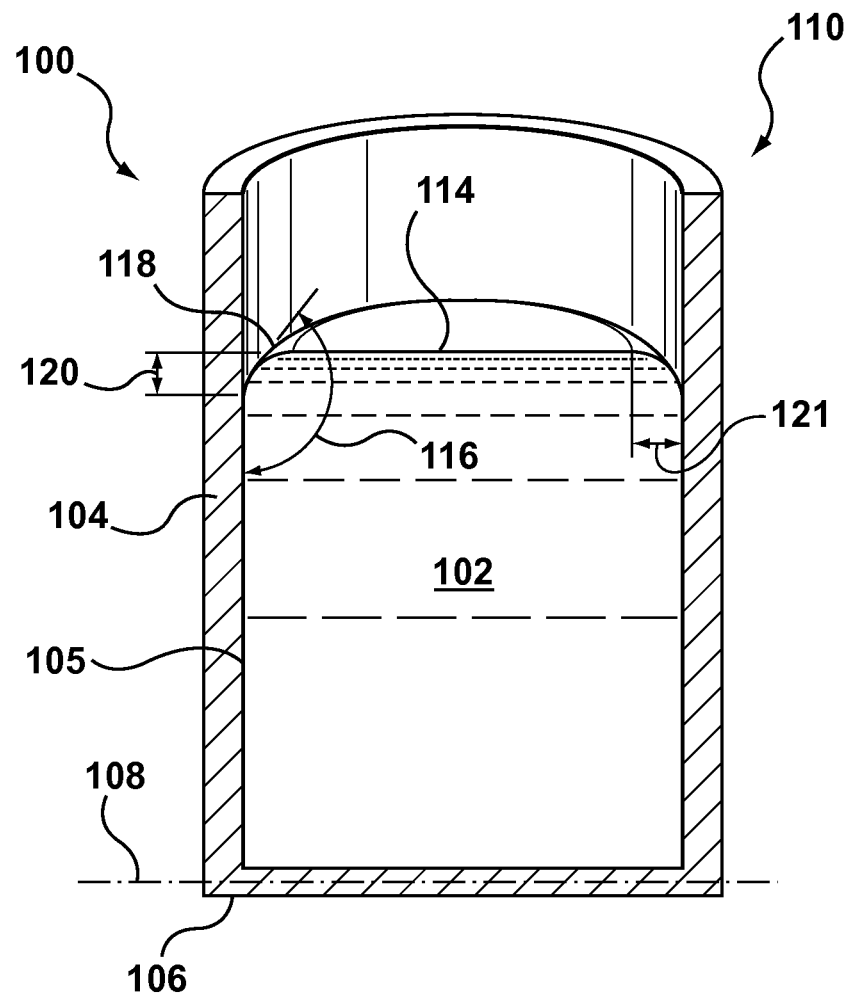
FIG. 1c is a cross-section view of a vessel containing a fluid having a contact angle greater than 90 degrees.

Referring to FIGS. 1a-1c, an example of a vessel 100 containing a liquid 102 is illustrated. For clarity and ease of description, in this application the vessel 100 is described as a cylindrical vessel or tube having a sidewall 104 and a bottom 106 discusses meniscus formation of the liquid in a cylindrical tube that comprises the solid phase. However, it is understood that the vessel 100 may be any suitable shape (e.g. square, round, or triangular tubing, wells, or other containers) and may have a greater or fewer number of sidewalls 104 (for example a square container could have four orthogonal sidewalls). While the vessel sidewalls 104 are illustrated as being vertical, it is understood that in some examples at least a portion of each sidewall 104 may be inclined, curved or otherwise shaped. The sidewalls 104 further comprise an inner or interior surface 105 for contacting the liquid 102 retained in the vessel 100.

In the present example the vessel bottom 106 is flat, as illustrated, while in other examples the vessel bottom 106 may be sloped, concave, convex or any other suitable shape. Regardless of the actual shape of the vessel bottom 106, the vessel 100 defines a lower plane 108 that is spaced apart from the end of the vessel 110 and intersects the vessel sidewalls 104 at the same orientation as a flat vessel bottom 106. In the present example the vessel bottom 106 lies within the lower plane 108. In other examples having non-flat bottoms, the vessel bottom 106 may not coincide with the lower plane 108.

The vessel 100 may be constructed from any material that is suitable for the introduction of micro-surface topologies or the application of hydrophilic, hydrophobic and superhydrophobic surface coatings. Examples of suitable materials include polymeric materials, polystyrene, polypropylene, polycarbonate, polyvinylchloride, polytetra-fluoroethylene, or other suitable polyolefin. The hydrophobic coating materials could for example be silicone based, fluoropolymer based, petroleum jelly, or paraffin wax. Superhydrophobic coatings could consist of nanostructured films, for example films of nanotubes composed of silica, carbon, or perfluorocarbon polymers. Such coatings are known in the art as nanotube "carpets", "forests", or "films". Nanostructured films could also consist of other regularly or irregularly organized molecular assemblies resulting in nanofeatured surfaces.

As exemplified, the vessel 100 is configured to retain a volume of liquid 102. The liquid 102 has a free surface or upper surface 114 that has a liquid surface tension. The properties and characteristics of the liquid surface tension may depend on the composition of the liquid. Examples of liquids 102 that may be contained within the vessel 100 include aqueous solutions of salts, sugars, proteins, glycoproteins, polysaccharides, methylcellulose, agar, collagen, or other similar gelling agents.

At the interface between the interior surface 105 of vessel sidewall 104 and the free surface of the liquid 114, the peripheral portions of the liquid surface may engage the interior surface 105 of the vessel 100 at a different level within the vessel 100 than the free surface level 114. The difference in surface level between the free surface 114 and the liquid-sidewall interface is referred to as meniscus 118 having a meniscus magnitude 120. The distance from the interior surface 105 to the point where the liquid surface 114 is essentially planar is the meniscus width 121. The angle between the vessel side wall 104 and the liquid surface in the meniscus 118 region defines a contact angle 116. If the contact angle 116 is less than 90 degrees, as shown in FIG. 1a, the meniscus is considered a concave meniscus 118. If the contact angle is greater than 90 degrees, as shown in FIG. 1c, the meniscus is considered a convex meniscus 118. If the contact angle is equal to 90 degrees, as shown in FIG. 1b, the meniscus magnitude 120 (shown in FIGS. 1a and 1c) is zero, the meniscus width 121 is zero, and the liquid is described as having no meniscus 118.

Figure 2:
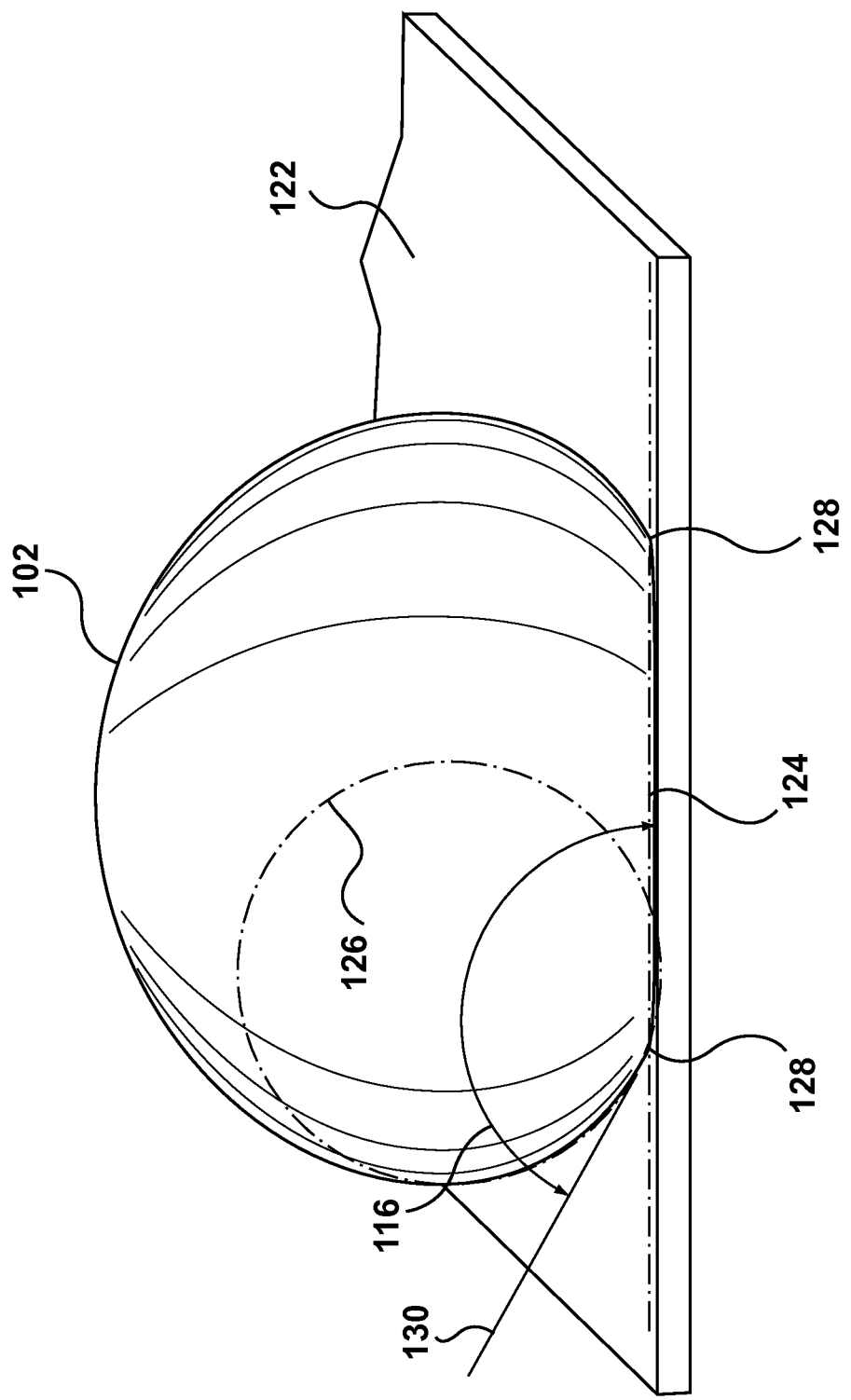
FIG. 2 is an image of a liquid droplet on a surface defining a contact angle.

One example of a method for measuring the contact angle 116 between a liquid 102 and a solid surface 122 is described with reference to FIG. 2. FIG. 2 illustrates a drop of liquid 102 resting on a substantially horizontal surface 122. In order to quantify contact angles 116 at the three-phase (solid substrate-aqueous liquid-air) interfaces, a 20 µL droplet of the liquid 102 was slowly placed onto the surface 122. Lateral view images of the droplet 102 resting on the surface were captured with the use of a Lumenera digital camera and a 0.6× magnification lens. The lens was oriented horizontally facing the drop 102, at a level even with the solid surface 122. Illumination was provided by backlighting with an amber LED behind an opaque diffuser. Image capture conditions were maintained at constant settings (Gain 1, exp. 0.3 s, acquisition resolution 2080×1536). The dynamic minimum contact angles 116 were determined by image capture after increasing the droplet volume to 40 µL and then removing 20 µL to recede the contact line over the surface. Images were captured within 2 to 5 seconds of droplet 102 manipulation.

The contact angle 116 was determined by analysis of lateral view images. Briefly, the horizontal plane (droplet baseline) of the image was established by drawing a straight line 124 through the contact points of the droplets with the surface 122. A best fit circle 126 is drawn through perimeter points of the droplet 102 near the contact points 128 of the left and right margins of the droplet 102 with the surface. This circle 126 is intended to be a best fit to the curvature of the surface of the droplet 102 near the contact point 128. The angle between 124 and the tangent line 130 to the best fit circle 126 at contact point 128 is taken to be the contact angle 116.

For a given liquid/solid interface (i.e. the interface between liquid 102 and sidewall 104), the magnitude of the meniscus 120 formed may be altered by modifying the contact angle 116 created between the liquid 102 and the sidewall 104. The present application relates to a meniscus reducing member that physically alters the contact angle 116 formed between liquid 102 and the meniscus reducing member so that the contact angle 116 between the liquid 102 and the meniscus reducing member is closer to 90 degrees than the contact angle 116 between the liquid 102 and the original sidewall 104 material. Reducing the meniscus magnitude 120 by altering the contact angle 116 between the liquid 102 and the sidewall 104 may be understood as compensating for the contact angle effects or compensating for the contact angle between the liquid 102 and a surface.

Referring to FIGS. 3-12, described below are examples of a meniscus reducing member 132 for use in a vessel 100 for containing a liquid 102. Each meniscus reducing member 132 includes a surface feature 134 overlying at least a portion of an interior surface 105 of the vessel 100. Each example of the surface feature 134 includes at least two surfaces 136, 137 for contacting the liquid 102 in the vessel 100. The at least two surfaces 136, 137 cooperate to reduce a magnitude of a meniscus 120 and meniscus width 121 (shown in FIGS. 1a and 1c) formed at an interface between the liquid 102 and the surface feature 134 by physically altering or compensating for the contact angle 116 between the liquid 102 and the surface feature 134.

Referring to FIGS. 3-6, a first example of a vessel 100 including a meniscus reducing member 132 is illustrated. In this example, the meniscus reducing member 132 includes a surface feature 134 which include a step-like feature in which the at least two surfaces 136, 137 include the first and second inner faces 138, 140 and a generally upward facing step face 142 (in this application "upward", "upper" and other similar terms are generally used to refer the direction toward the open, end of the vessel 110).

The step face 142 extends between and connects the first and second inner faces 138, 140, and a step edge 144 is defined by the intersection of the second inner face 140 and the step face 142. In some examples, shown in FIGS. 3 and 5, the step face 142 is generally flat, upward facing surface that is generally perpendicular to the first and second inner surfaces 138, 140. In other examples, as shown in FIGS. 4 and 6, the step face 142 is an angled or sloped surface, that is at an oblique angle to the first and second inner surfaces 138, 140, having a slope angle 148.

Meniscus formation may be inhibited (i.e. the contact angle 116 may approach 90 degrees and the meniscus magnitude 120 may approach zero) by introducing the single-step or step-like surface feature 134 at a given position around the inner perimeter of the interior surface 105 surface of the vessel 100. In this case, the step-like surface feature 134 is located toward the end 110 of the vessel 100. In other examples, the surface feature 134 may be located in other positions within the vessel 100.

When a liquid contacts the step-like surface feature 134, as shown in FIGS. 3-6, the meniscus formed at the interface between the interior surface 105 and the liquid is diminished as the level of liquid in the container approaches the step edge 144 of the surface feature 134. To form a meniscus between the liquid 102 and the vessel 100, the liquid 102 must be in physical contact with the interior surface 105 of the vessel 100; the meniscus magnitude 120 (shown in FIGS. 1a and 1c) cannot exceed the distance between the free surface of the liquid 114 and the end of the vessel 110. The step-like surface feature 134 acts as a virtual or imitation upper edge of the vessel. As the surface level of the liquid 102 increases within the vessel 100, the distance between the liquid surface the step edge 144 and step face 142 decreases, thereby reducing the available portion of the second inner surface 140 that can support the meniscus. When the position of the free surface of the liquid contained in the vessel is equal to the position of the step edge 144, a flat liquid-vapor interface (i.e. a contact angle of 90 degrees) will result, regardless of the intrinsic contact angle 116 of solid-liquid-vapor interface (i.e. the contact angle 116 between the liquid 102 and a flat surface 122 made from the surface feature 134 material).

Figure 4:
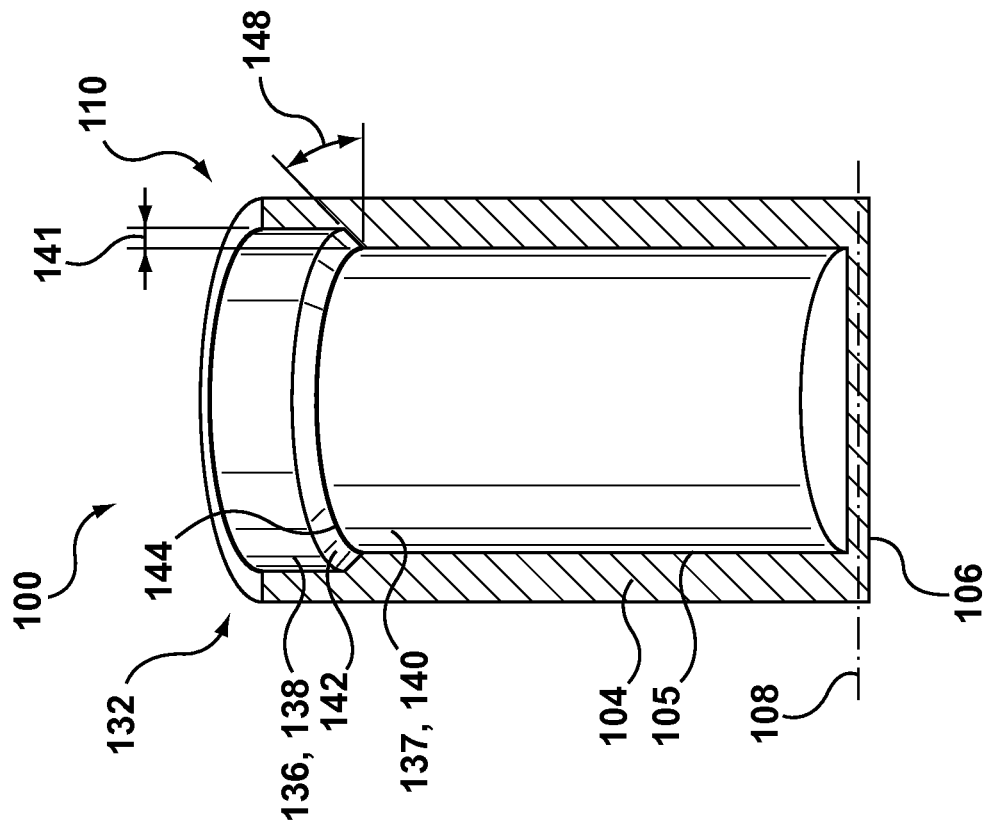
FIG. 4 is a cross-section view of a vessel including a meniscus reducing member having a sloped step-like surface feature.

In examples where the step face 142 is a sloped step face 142, as shown in FIGS. 4 and 6. The meniscus magnitude 120 may be reduced due to compensation of the intrinsic contact angle 116 of the 3-phase contact line by the slope of the step face 142, represented by angle 148. The slope angle 148 may be between 0 and 75 degrees, and in the present example the slope angle 148 is 45 degrees.

The meniscus reducing capability of the step-like surface feature 134 is most effective when the free surface of the liquid is generally level with the step edge 144 or some part of the sloped step face 142. If the free surface of the liquid is level with the step edge 144 then the tangent line 130 (as shown in FIG. 2) will be parallel to the step edge 144.

Figure 3:
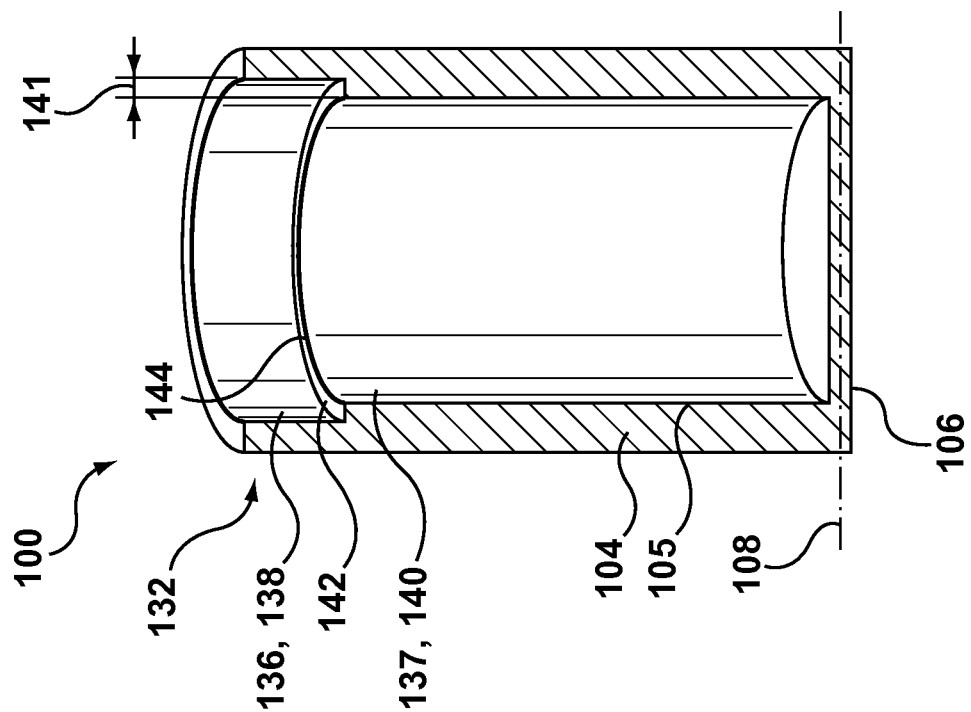
FIG. 3 is a cross-section view of a vessel including a meniscus reducing member having a flat step-like surface feature.

In the present example, the first and second inner faces 138, 140 are generally orthogonal to the lower plane 108 (i.e. generally vertical when the vessel is in an upright position) and the second inner face 140 is inwardly offset from the first inner face 138 by an offset distance 141 (shown in FIG. 3). The offset distance 141 may be greater than 0.1 mm and in the present example is about 2 mm. Both the first and second inner faces 138, 140 have a generally annular shape and are concentrically aligned.

In some examples, as illustrated in FIGS. 3 and 4, the surface feature 134 may be integral with the vessel 100 and the first and second inner faces 138, 140 and the step face 142 may be integral with, and form a portion of, the interior surface 105 of the sidewall 104.

In other examples, as illustrated in FIGS. 5 and 6, the meniscus reducing member 132 may be provided as a separate insert member 146, in this example an annular or ring-like insert member 146, that is sized to fit within a complementary vessel 100 so that the surface feature 132 overlies at least a portion of the vessel's 100 interior surface 105 and contacts the liquid. The insert member 146 may be made from any suitable material as described herein, and need not be the same material as the surrounding vessel 100. For example, a polymeric insert member 142 may be received within a glass test tube, beaker, vial or other vessel 100. It is understood that the overall shape and dimensions of the insert member 146 may be chosen based on the shape and size of a particular vessel 100.

In some examples, the surface feature 134, in this example the first and second inner faces 138, 140, step face 142 and step edge 144, extends around the entire inner perimeter of the interior surface 105. In other examples, the surface feature 134 extends only part way around the inner perimeter of the interior surface 105 (see, for example, FIG. 7a). While the step faces 142 illustrated are substantially planar, in some examples the step faces 142 may be curved or otherwise non-planar surfaces.

Suitable materials for constructing the step-like surface feature 134, either as an insert 146 or an integral portion of the vessel 100, include polystyrene, polypropylene, polycarbonate, polyvinylchloride polytetra-fluoroethylene, silicone, EPDM (ethylene propylene-diene monomer), Buna Nitrile and ultra-high molecular weight (UHMW) plastic.

In one experimental example UHMW inserts exhibiting various surface topologies were constructed, including insert members 146 including step-like surface features 134. The inserts were placed into wells of polystyrene 6-well tissue culture plates (Costar 3516) (not shown) and a sufficient volume of MethoCult was dispensed into the well such that the liquid surface was level with the step edge 144 of the step-like surface features 134. Brightfield images of the surface of MethoCult medium at the interface with the surface feature were acquired for measurement of meniscus magnitude.

The effects of the inserts' surface topologies on the meniscus magnitude are summarized in Table 1. Use of an unfeatured insert resulted in a significant reduction of meniscus width 121 (as shown in FIGS. 1a and 1c) to about 50% compared to the untreated polystyrene culture wells surface. Of the step-like surface features 134, the flat step face 142, as shown in FIGS. 3 and 5, produced a 40% reduction of meniscus magnitude relative to the unfeatured insert control, and the sloped step face 142 configuration, as shown in FIGS. 4 and 6, eliminated the observable meniscus (i.e. there was no observable meniscus created using the sloped step face 142).

When the level of the liquid was increased above the step edges 144 of the surface features 134, a distinct liquid/solid interface and a background of even intensity was observable due to the opaque nature of the plastic inserts.

TABLE 1

Effect of inserts on meniscus magnitude, with the liquid level at the lower edge of the inserts.

| Insert | Meniscus Width (mm) |
| --- | --- |
| Untreated, no insert | 2.2 |
| Unfeatured insert | 1.2 |

TABLE 1-continued

Effect of inserts on meniscus magnitude, with the
liquid level at the lower edge of the inserts.

| Insert | Meniscus Width (mm) |
|---|---|
| Flat-step insert | 0.7 |
| Sloped-step insert | 0.0 |

Referring to FIGS. 7-10, another example of a meniscus reducing member 132 is illustrated comprising a surface feature 134 that includes a corrugated member 150 in which the at least two surfaces 136, 137 include a plurality of pairs of converging first and second surfaces 152, 154. Each pair of first and second surfaces 152, 154 intersect to define an edge 156. While in the present example the edge 156 is illustrated as forming a sharp peak, in other examples the edge 156 may be rounded, curved, chamfered, angled and may provide a smooth transition between the first and second surfaces 152, 154.

The first surfaces each have a first slope, defined by a first slope angle 158 and the second surfaces each have a second slope, defined by a second slope angle 160. In some examples the first and second slopes have slope angles 158, 160 between 1 and 75 degrees. In other examples, the first and second slopes have slope angles 158, 160 between 5 and 60 degrees. The specific slope angle chosen can be based on the material of the surface feature 134, the composition of the liquid to be received in the vessel 100 and the desired contact angle 116.

In some examples, the first and second surfaces 152, 154 may have generally the same size and the same slope angle 158, 160. In other examples, the first slope is different than the second slope and the first and second surfaces 152, 154 may have different slope angles 158, 160.

Figure 10:
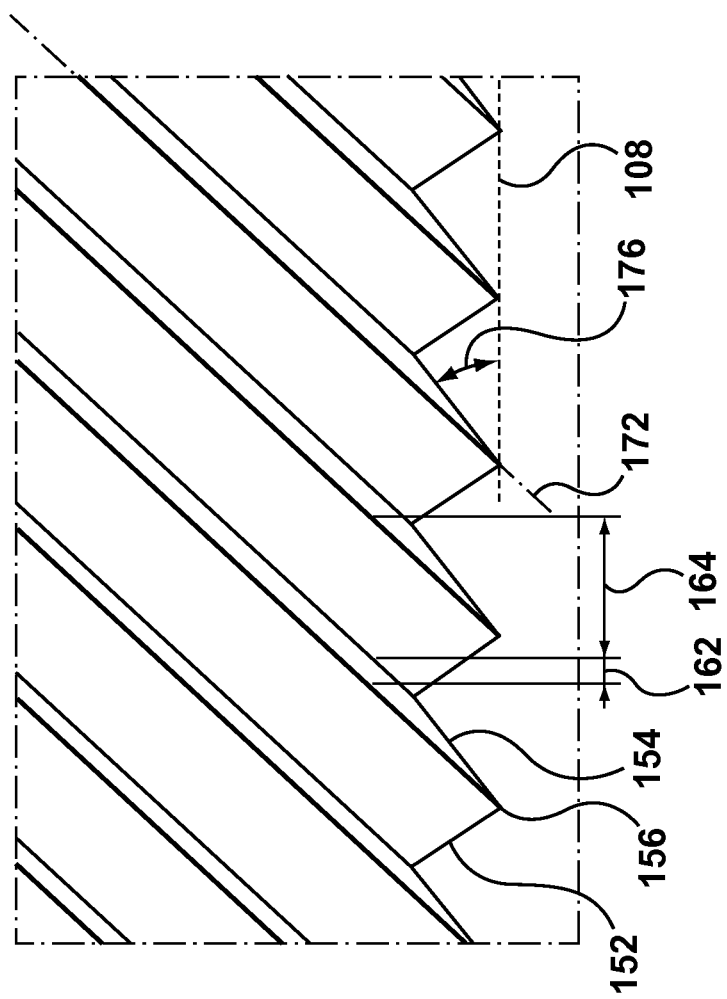
FIG. 10 is a side view of another example of a corrugated member.

As best shown in FIGS. 8-10, the first and second surfaces 152, 154 have respective surface widths 162, 164. In some examples, as shown in FIG. 8, the surface widths 162, 164 may be equal. In other examples, as shown in FIG. 9, the surfaces widths 162, 164 may be different.

Figure 7:
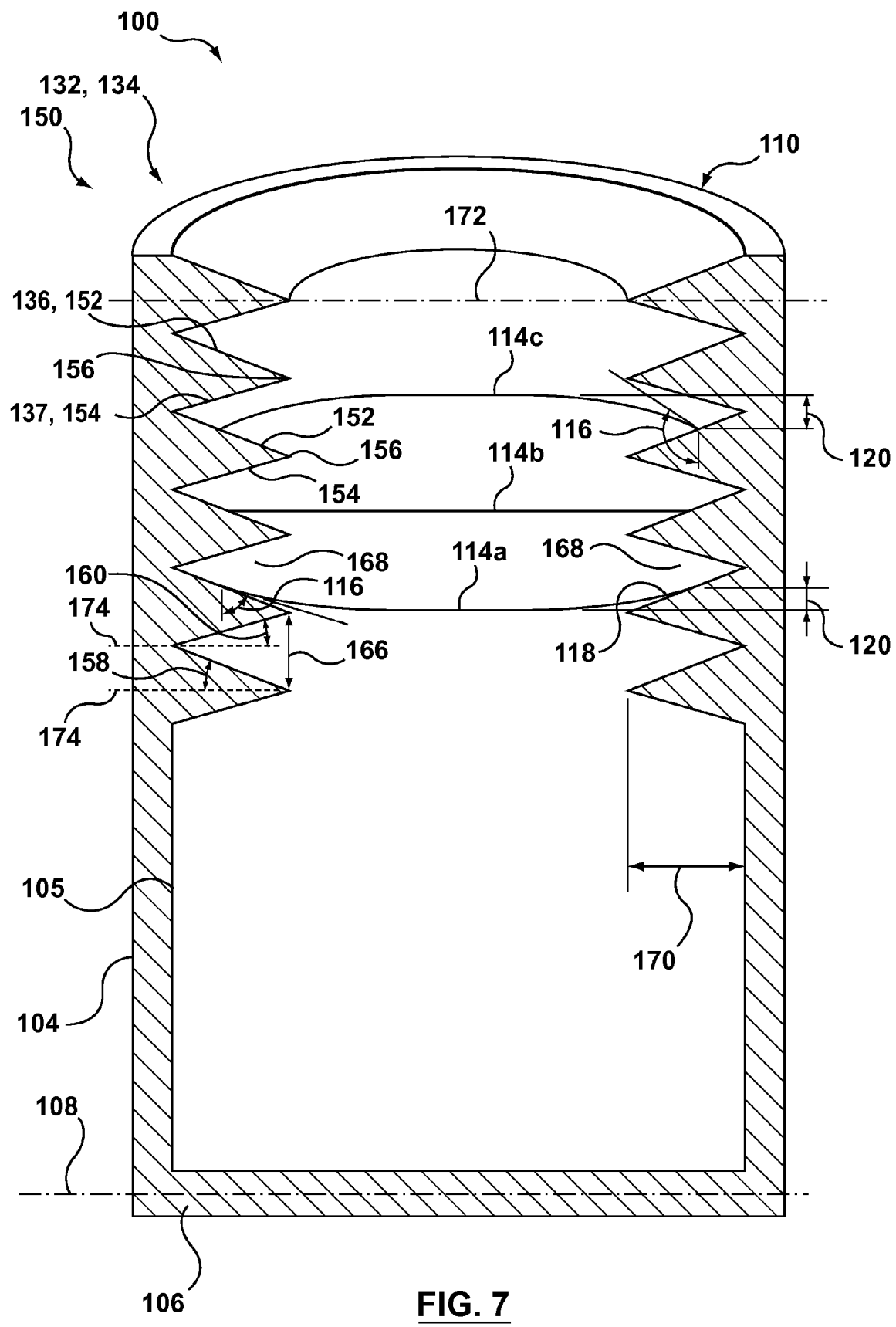
FIG. 7 is a cross-section view of a vessel including a corrugated meniscus reducing member.
Figure 7A:
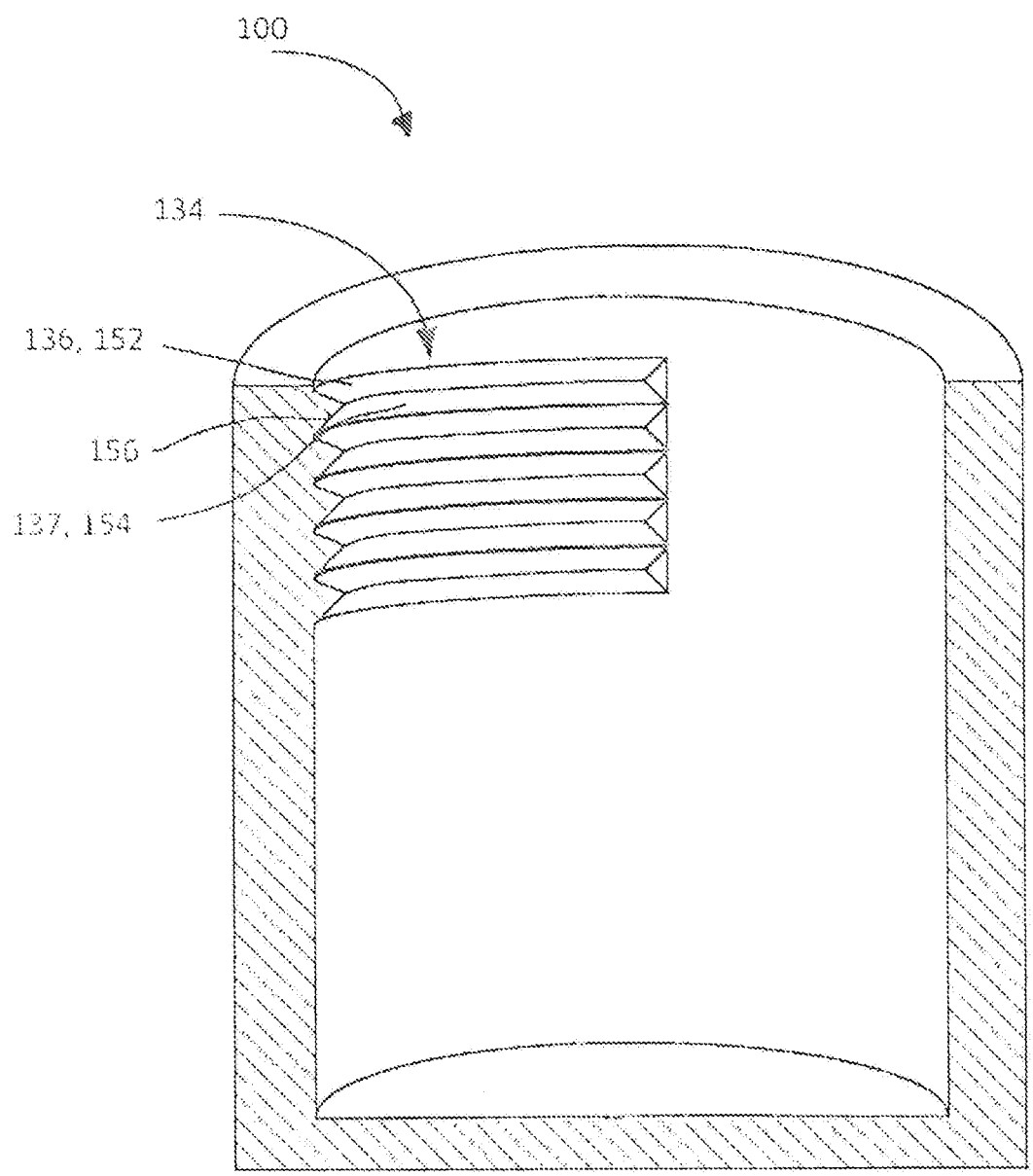
FIG. 7a is a cross-section view of a vessel including a corrugated meniscus reducing member extending only part way around an inner perimeter of the vessel.

The edges 156 of corrugated member 150 also have an edge height 170, as shown in FIG. 7. In some examples, the edge height 170 is between 0.01 and 1.5 mm.

Adjacent edges 156 of the corrugated member 150 are spaced apart or separated by an edge spacing distance 166. In some examples, the particular peak spacing distance 166 used in a given corrugated member 150 can be set to prevent wetting of the first and second surfaces 152, 154 by the liquid due to the surface tension of the liquid. That is, the edge spacing distance 166 is small enough to inhibit penetration of the liquid into the valleys or spaces 168 between opposing first and second surfaces 152, 154 due to the energy required to overcome the surface tension of the liquid at the liquid-vapor (LV) interface (not shown). If the solid surfaces, i.e. the first and second surfaces 152, 154 are sufficiently hydrophobic, then given a sufficiently small edge spacing distance 166, the contact of the liquid with the first and second surfaces 152, 154 would be expected to be limited to the edges 156. As such, the liquid is in the Cassie-Baxter state and exhibits a greater contact angle 116 and mobility at the solid surface than if the surface was completely wetted. In some examples the edge spacing distance 166 is between 0.01 and 5 mm and in other examples the edge spacing distance 166 is between 0.01 and 3 mm.

The repeating pattern of pairs of first and second surfaces 152, 154 and edges 156 mitigate the meniscus magnitude 120 by compensating for the dynamic minimum contact angle formed at the three-phase interface and by physically limiting the rise or fall of the liquid-vapor surface due to the contact angle.

The first and second surfaces 152, 154 of the corrugated member 150 may also reduce the meniscus formed in the vessel 100 by compensating for acute contact angles 116 with the surface of the fluid 114. In some examples, the slopes of the first and second surfaces 152, 154 of the corrugated member 150 may be constant to form flat surfaces at alternating slope angles 158, 160 ($\theta_R$ and $\theta_F$). In other examples, the slope may be variable to form surfaces 152, 154 with an undulating or curved surface.

For the purpose of this explanation, the slope and angles 158, 160 are measured relative to horizontal plane, for example planes 174 parallel to the lower plane 108 of the vessel 100. In this application, the first surface 158 is also referred to as a rising surface, since the liquid contact advances over the first surface 152 as the liquid level within the vessel 100 rises. Accordingly, for the purposes of Equation 1 below, the first slope angle 158 is referred to as the slope of the rising surface $\theta_R$. Similarly, the second surfaces 154 are also referred to as falling surfaces since liquid contact advances over the bottom of the surface as the liquid level increases, and the second slope angle 160 is also referred to as the slope of the falling surface $\theta_F$. The slope angles 158, 160, also referred to as angles $\theta_R$ and $\theta_F$ respectively may be of any value between 0 and 90 degrees.

The corrugated member 150 also has a surface feature axis 172. In some examples, as shown in FIG. 7, the surface feature axis 172 extends horizontally, parallel to the lower plane 108. FIGS. 8-10 illustrate examples of the first and second surfaces 152, 154 of the corrugated member 150. The converging pair of first and second surfaces 152, 154 together with the corresponding edge 156 can also be referred to as a corrugation. In the examples shown in FIGS. 8-10, the surface feature axis 172 extends along a longitudinal length of the corrugations; a direction that is generally orthogonal to the surface widths 162, 164. In FIGS. 8 and 9, the corrugate member 150 is aligned such that the surface feature axis 172 would be parallel to the lower plane 108 of the vessel 100. In FIG. 10, corrugated member 150 is tilted so that the surface feature axis 172 is at an angle 176 relative to a lower plane 108 of the vessel, the angle 176 being between 0 and 90 degrees (i.e. the corrugations may range from horizontal or vertical).

The corrugations (i.e. pairs of converging first and second surfaces 152, 154 and the corresponding edge 156) reduce meniscus formation by compensating for or countering the contact angle effects at the liquid solid interface. For example, if the contact angle 116 (between the liquid and the material of the corrugated member) is less the first slope angle 158, $\theta_R$, as illustrated using example liquid surface 114a in FIG. 7, a concave meniscus 118 is formed as the three-phase contact line falls on a first or rising surface 152 having the slope angle 158, $\theta_R$. The three-phase contact line (not shown) is the line of contact between the liquid, solid, and vapour phases of a liquid in contact with a surface; in a liquid containing vessel 100, this is the contact line between the liquid 102 and the interior surface 105 of the vessel at the top or free surface 114 of the liquid 102.

If the contact angle is greater than $\theta_R$, as illustrated using liquid surface 114c in FIG. 7, a convex meniscus 118 is formed as the three-phase contact line falls on a first or rising surface 152 with slope angle 158, $\theta_R$. If the contact angle is equal to the first slope angle 158, $\theta_R$, illustrated as liquid surface 114b in FIG. 7, no meniscus is likely to form due to the compensation or counteracting effect of combining the contact angle 116 by the first surface angle 158.

If the liquid surface 114 is positioned such that the liquid/corrugated member contact line resides on a second or falling surface 154 (not shown), a concave meniscus is expected if the contact angle 116 is less than 180 degrees–$\theta_F$, no meniscus is expected if the contact angle is equal to 180 degrees–$\theta_F$, and a convex meniscus is expected if the contact angle is greater than 180 degrees–$\theta_F$.

One example of a corrugated member 150 may be created having an edge height 170 0.5 mm, first and second slope angles 158, 160 having an equal slope of 15°, and edge spacing distance 166 of 268 μm. An aluminum mold with such a surface topology may be constructed by CNC machining. Castings of this corrugated member were created with PDMS polymerized in the mould to create hydrophobic surfaces exhibiting the desired, corrugated topology. Strips with a width of 10 mm were then cut from the PDMS casts with the corrugations either parallel to the long axis of the strip, or oriented at a 45° angle (176, λ). The strips were then inserted into 35 mm culture wells (not shown) to cover the interior surface 105 of the well walls 104 with the corrugated member 150. The effect on meniscus width 121 was evaluated by placing a 2 mL volume of a protein containing liquid medium (Iscove's Modified Eagle Medium (IMDM) with 2% human serum albumin) into the well and tilting and rotating the well to advance and retreat the liquid level over the wall surface. The meniscus width was determined by brightfield microscopy.

Meniscus width was determined by acquiring brightfield images of the liquid surface of test solutions at the interface with the walls of the culture dishes. The images were acquired using an inverted microscope (Zeiss Axiovert™ 40 CFL) and a Lumenera digital camera through a 2.5× magnification objective and 1× camera ocular. The magnitude of the meniscus width was determined by spatial calibration of these images and measurement of the dark area using digital image processing methods.

Optical interference resulting from the meniscus was quantified by integration of the intensity profile of the dark area corrected for image brightness using images acquired above. Optical interference is stated as a percentage normalized to the integrated pixel intensity values obtained for the meniscus formed by MethoCult (1% methylcellulose/IMDM) in an untreated polystyrene dish.

The effect of corrugated member 150 on meniscus width 121 is presented in Table 2. While a meniscus with a width 121 of 2.5 mm was observed when a well sidewall (not shown) is lined with unfeatured (i.e. non-corrugated member) PDMS, the meniscus magnitude was eliminated when the corrugation member described above was included on the PDMS surface. When the surface feature axis 172 was set a 45° angle 176 from the horizontal plane, an undulating meniscus pattern of reduced magnitude was observed.

TABLE 2

Effect of corrugated member on meniscus width.

| Topology | Meniscus Width (mm) |
| --- | --- |
| Untreated, no insert | 2.9 |
| Unfeatured PDMS insert | 2.5 |
| Horizontal corrugations | 0.0 |
| 45° angled corrugations | 0.3 |

When the surface feature axis 172 and corrugations (combining 152, 154, 156) are oriented in a horizontal direction relative to the interior surface 105 of the vessel 100, contact angles 116 will be compensated by the surface slope 158 on rising (first) surfaces 152 resulting in a reduction of meniscus width 121 and magnitude 120. However, contact angles 116 may be exacerbated (moved further from 90 degrees) by the slope 160 on falling (second) surfaces 154. Therefore, with the exception of contact angles 116 exceeding 180 degrees–$\theta_F$, the meniscus limiting effects of corrugated surfaces may be most useful when the liquid surface 114 is adjusted to contact the rising (first) surfaces 152.

With most polymeric surfaces and aqueous solutions, the expected contact angles 116 are less than 90 degrees. Accordingly, one configuration of the corrugated member 150 for meniscus reduction includes of a first slope 158, $\theta_R$ that is equal to the expected contact angle 116 and a second slop 160, $\theta_F$ that is equal to 0 degrees (i.e. a second (falling) surface 154 having a width 164 of 0). In such a configuration, meniscus magnitude 120 is diminished at several locations on the corrugated member 150, except for the edges 156.

Another configuration of corrugated member 150 is created when the surface feature axis 172 is at an angle 176 (also described as λ for the purposes of equation 1), as shown in FIG. 10. In such examples, the surface slope angle 158, 160 at any given three-phase contact point is the vector perpendicular to the first or second surface 152, 154 at that contact point (illustrated as 128 in FIG. 2). The component of the vector (not shown) that lies in the horizontal plane (parallel to the lower plane 108), and contributes to contact angle 116 compensation in that plane, is diminished as the angle 176, λ increases. When the angle 176, λ equals 90 degrees, neither of first and second surfaces 152, 154 lie in the horizontal plane, and no meniscus compensation is expected.

When the corrugations are oriented at an angle to the vertical plane (perpendicular to the lower plane 108, not shown), the 3-phase contact line traverses alternately across rising and falling surfaces 152, 154, resulting in alternating contact angles 116 as a result of the compensation on rising surfaces 152 and exacerbation on the falling surfaces 154 described above. The effect on these contact angles 116 is limited to the vector of the slope angle 158, 160 that lies in the horizontal plane. As the angle 176, λ increases, the length of the alternating contact angle 116 regions decreases and undulations in the meniscus 118 exhibit a shorter period. At a given angle 176, λ, the undulations are expected to cancel, resulting in a flattened meniscus 118.

The weighted average contact angle can be used to describe the expected effective contact angle resulting from the undulations. A weighted average contact angle of around 90 degrees would suggest that there was no meniscus. The weighted average contact angle is a function of the proportion of the solid-liquid-vapor contact line contacting the rising surfaces 152 and the proportion of the solid-liquid-vapor contact line contacting the falling surfaces 154. The weighted-average contact angle of the liquid can be represented mathematically by equation 1:

Equation 1

Weighted average contact angle =

Proportion of contact line on rising surface * compensated contact angle on rising surface + proportion of contact line on falling surface * exacerbated contact angle on falling surface =

$$[D_R \div (D_R + D_F) * (A_R + (\theta_R * (90 - \lambda)/90)] + [D_F \div (D_R + D_F)) * ((A_F + (\theta_F * (90 - \lambda)/90) - 90)]$$

where:

$D_R$ = width of rising surface interval in contact with liquid at the liquid-vapor surface $D_F$ = width of falling surface interval in contact with liquid at the liquid-vapor surface $A_R$ = intrinsic contact angle of the liquid on the rising surface $A_F$ = intrinsic contact angle of the liquid on the falling surface $\theta_R$ = slope of the rising surface of corrugations $\theta_F$ = slope of the falling surface of corrugations $\lambda$ = slope of the corrugations from the horizontal A net meniscus reduction over the entire corrugated member 150 is expected as angle 168, $\theta_F$ decreases and as angle 158, $\theta_R$ increases. Also, as angle 176, $\lambda$ increases towards 90 degrees, the weighted contact angle (and hence meniscus reduction) is decreased due reduced proportion of the vectors of the angles in the horizontal plane. However, the meniscus reduction effect of angle 176, $\lambda$ is a factor of both the reduced weighted contact angle with increasing angle 176, $\lambda$ and the reduced frequency of the intervals with increasing angle 176, $\lambda$.

Therefore, one example of the corrugation member 150 for use with aqueous solutions has a rising surface slope angle 158 of 60 to 80 degrees and a falling surface slope angle 160 of 0 degrees, with a surface feature axis slope angle 176, $\lambda$ of 45 degrees.

Figure 11:
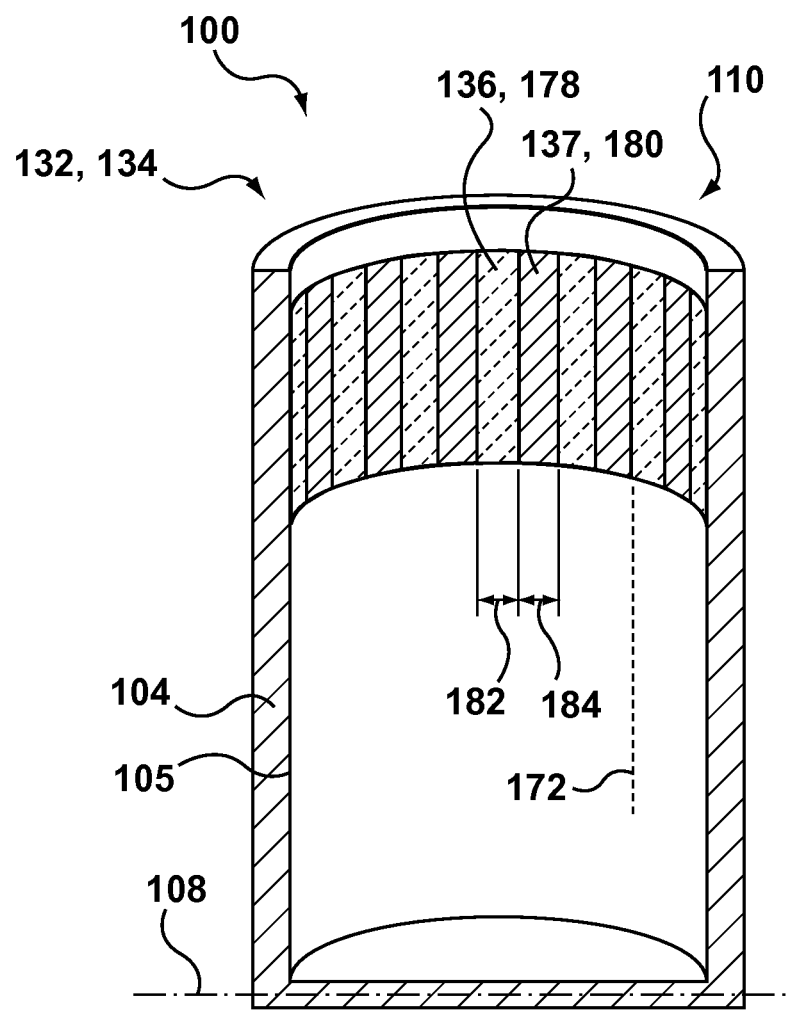
FIG. 11 a cross-section view of a vessel including a meniscus reducing member having a vertical striated surface feature.
Figure 12:
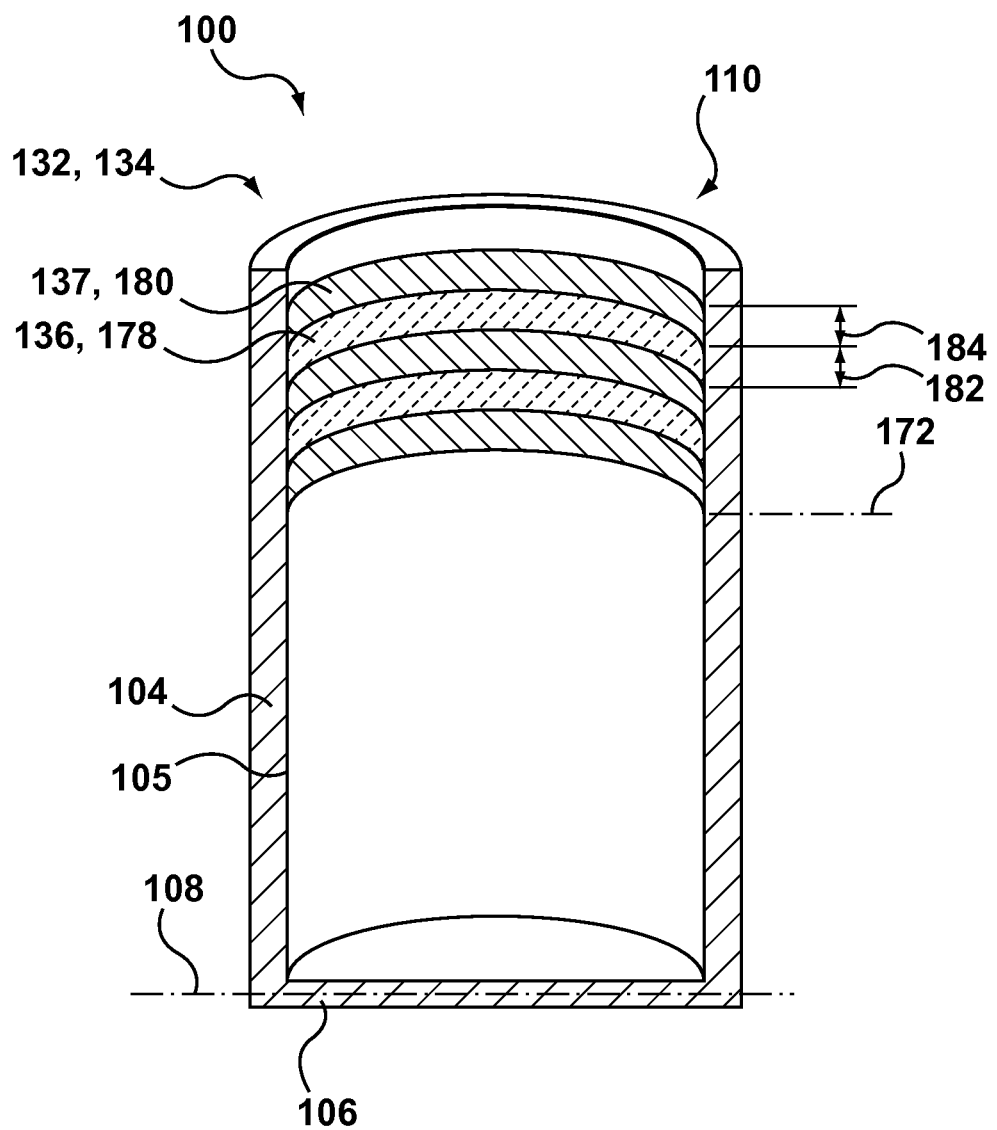
FIG. 12 is a cross-section view of a vessel including a meniscus reducing member having a horizontal striated surface feature.
Figure 13:
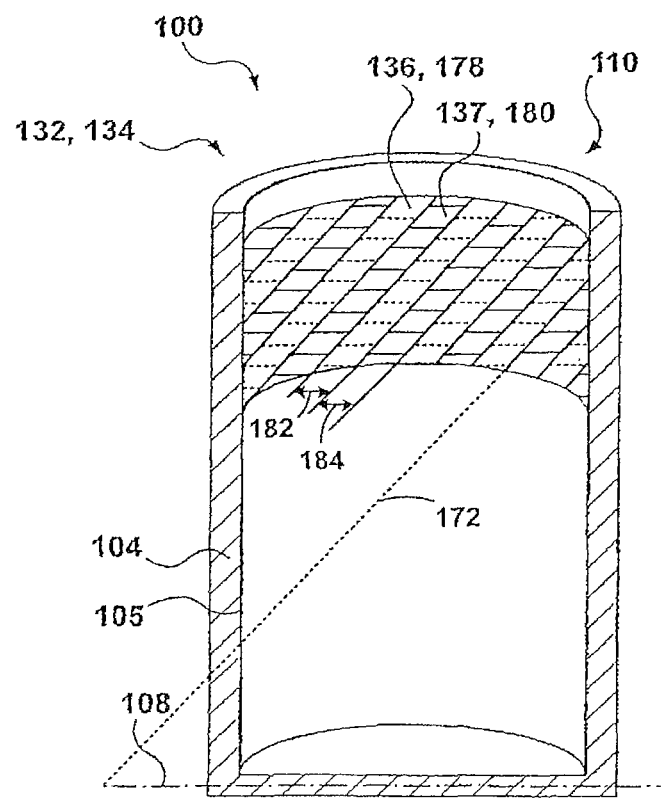
FIG. 13 is a cross-section view of a vessel including a meniscus reducing member having an angled striated surface feature.

Referring to FIGS. 11-12, another example of a meniscus reducing member 132 is illustrated having a surface feature 134 in which the at least two surfaces 136, 137 include a plurality of alternating first and second surface regions 178, 180. Each of the first surface regions 178 has a first surface energy and each second surface region 180 as a second surface energy. The second surface energy is different than the first surface energy thereby creating an alternating arrangement of different surface energies.

In this application, the term surface energy relates to the relative hydrophobicity or hydrophilicity of the surface. A surface is considered hydrophilic if the surface that exhibits a contact angle 116 with an aqueous liquid of less than 90 degrees. A surface is considered hydrophobic if the surface that exhibits a contact angle with an aqueous liquid of greater than or equal to 90 degrees and less than or equal to 150 degrees. A surface is considered superhydrophobic if the surface that exhibits a contact angle with an aqueous liquid of greater than 150 degrees. Because of the influence of the liquid composition, a surface may be considered hydrophobic with one aqueous solution, but may be considered hydrophilic with a different solution.

In this example of the meniscus reducing member 132, the alternating pattern of first and second surface regions 178, 180 create a striated pattern of different surface energies. In this example, the alternating first and second surface energies have different relative surface energies leading to a pattern of alternating hydrophilic and hydrophobic or superhydrophobic surface regions. In some examples the first surface region 178 is hydrophilic and the second surface region 180 is hydrophobic, or superhydrophobic. In other examples, the first surface region 178 is hydrophobic and the second surface region 180 is superhydrophobic (which may still create the desired relative difference in hydrophobicity).

Providing regions 178, 180 of varying hydrophobicity/hydrophilicity creates regions of alternating or varying contact angles. The frequency of these alternating contact angles is determined by the widths 182, 184 of the first and second surface regions 178, 180. Adjusting this frequency, which produces contact angle compensation between alternating concave and convex menisci, tends to result in a reduced meniscus magnitude and meniscus width that presents reduced optical interference for imaging.

In some examples each of the first and second region widths 182, 184 is between 0.01 and 5 mm and the first region width 182 is equal to the second region width 184. In other examples the first region width 182 is different than the second region width 184. In some examples where the first and second region widths 182, 184 are different the second region width 184 is greater than the first region width 182. In such examples the second region width 184 may be between 0.1 mm and 5 mm and the first region width 182 may be between 0.01 and 3 mm, while still being smaller than the chosen second region width 184. In some examples the first and second region widths 182, 184 are between 0.1 mm and 1 mm.

In some examples, the alternating first and second surface regions 178, 180 are spaced apart from each other by a region spacing distance that is between 0.01 and 3 mm.

The striated surface feature 132 also has a surface feature axis 172 that extends in the same direction as the striated surface regions 178, 180 (what would be considered the longitudinal direction if the first and second surface regions 178, 180 extended along a flat substrate, instead of following the inner surface 105 of the vessel 100). In some examples, the surface feature axis 172 is positioned parallel to the lower plane 108 of the vessel 100, as shown in FIG. 12. In this configuration, the striated surface feature 134 provides a plurality of alternating first and second surface regions 178, 180 along the vertical direction. In other examples, similar to the position of the corrugated member 150 above, the surface feature axis is oriented at a fixed, oblique angle relative to the lower plane of the vessel 100 (not shown). This angle may range from 0 degrees (parallel to the lower plane 108, as shown in FIG. 12) to 90 degrees (vertical, perpendicular to the lower plane 108, as shown in FIG. 11).

When the striated surface feature 134 is vertically oriented, as shown in FIG. 11, the three-phase contact line contacting the first and second surface regions 178, 180 experiences alternating convex and concave meniscus areas, corresponding to contact with hydrophobic/superhydrophobic areas and hydrophilic areas, or alternating degrees of convexity corresponding to contact with hydrophobic and superhydrophobic areas. One model of the physical manifestation of a meniscus contacting such striated first and second surface regions 178, 180 is for the meniscus to assume a formation related to the weighted average contact angle over the three-phase contact line. The weighted average of contact angle is derived from the proportion of the solid-liquid-vapor contact line contacting the striations of higher surface energy (e.g. superhydrophobic striations) and the proportion of the solid-liquid-vapor contact line contacting the striations of lower surface energy (e.g. hydrophilic striations). This can be represented mathematically by equation 2:

Equation 2

Weighted average contact angle = proportion of contact line in superhydrophobic region * superhydrophobic contact angle + proportion of contact line in hydrophilic region * hydrophilic contact angle

For the case of striations perpendicular to the bottom surface, this can be expressed by the equation: $= [(W_{SH} \div (W_{SH} + W_h)) * \lambda_{SH}] + [(W_h \div (W_{SH} + W_h)) * \lambda_h]$ where:

$W_{SH}$ = width of hydrophobic/superhydrophobic striations $W_h$ = width of hydrophilic striations $\lambda_{SH}$ = contact angle of hydrophobic/superhydrophobic striations $\lambda_h$ = contact angle of hydrophilic striations When the weighted average contact angle approaches approximately 90 degrees, a diminished meniscus width 121 results. A wide range of combinations of alternating superhydrophobic coating striations (second regions 180) with less hydrophobic striations (first regions 178) and the widths 182, 184 of the striations may result in such contact angles approaching 90 degrees. As the contact angle with the hydrophilic (or less hydrophobic region, first surface region 178) ($\lambda_h$) region decreases, a meniscus reducing weighted average contact angle can be maintained by increasing the hydrophobicity (contact angle, $\lambda_{SH}$) of the hydrophobic/superhydrophobic region (second region 180), increasing the width 184 of the second surface regions 180 (the second width 184 is also represented as $W_{SH}$ for the purposes of equation 2), decreasing the width 182 of the first surface regions 178 (the first surface region width 182 is also referred to as $W_h$ for the purposes of equation 2), or a combination thereof.

For striations where the surface feature axis is parallel to the bottom plane 108 (as shown in FIG. 12), the meniscus magnitude 120 may be reduced because the meniscus forms on a given striation and is prevented from moving to the next striation because of the difference in surface energy. In this case the meniscus magnitude may be related to the width of the striations 184 and 182.

The effective average contact angle increases as the width of the hydrophilic regions decreases and the width of the hydrophobic regions increases. As the width of the hydrophilic striations approaches 0 mm, the effective contact angle approaches the contact angle of the superhydrophobic regions. As the width of the superhydrophobic regions approaches 0 mm, the effective contact angle approaches the contact angle of the hydrophilic regions. The points at which the effective contact angle is 90 degrees are predicted to result in a flat meniscus.

In one experimental example, superhydrophobic surfaces 180 were generated on polystyrene substrate (not shown) by applying a spray coating of WX2100 (Cytonix Inc) to a flat polystyrene sheet. The coating became adherent to the surface upon sufficient drying, and imparted a superhydrophobic quality to the surface resulting in a contact angle with water of greater than 150 degrees. A striated hydrophobic/superhydrophobic surface was generated by scoring the coated surfaces at regular intervals using a blunt metal edge. This process removed the superhydrophobic coating on these intervals, exposing the less hydrophobic polystyrene surface (first surface regions 178). Superhydrophobic second surface region 180 striations with a width of 1 mm and 2 mm, interrupted by hydrophobic first surface region 178 striations with a width of approximately 0.5 mm may be created in this manner.

The effect of hydrophobic/superhydrophobic striated surface regions 178, 180 pattern on contact angle and meniscus magnitude was evaluated using the striated first and second surface regions 178, 180, created using the techniques described above. Several aqueous liquids were evaluated, including deionized water, Iscove's Modified Eagle Medium (IMDM), phosphate buffered saline containing 2% human serum albumin (PBS/2% HSA), and IMDM containing 1% methylcellulose. The effect on contact angles was evaluated by placing a 30 uL drop of the liquid onto the surface including the first and second surface regions 178, 180. An additional 30 uL volume of the liquid was added to and then removed from the existing droplet to result in the formation of a receding contact angle of the droplet with the surface. Lateral view images of droplets were acquired from two perspectives: parallel to the striations (i.e. along the surface feature axis 172) and perpendicular to the striations (i.e. perpendicular to the surface feature axis 172). Contact angles were determined for the droplets at these orientations using the methods described above in relation to FIG. 2. In addition, aerial views of the droplet at a perspective of ~30 degrees were acquired to illustrate the effect of striations on the shape of the 3-phase contact line.

The effects of striations on contact angle with the various aqueous liquids are summarized in Table 3. In the parallel point of view (POV), the 3 phase contact line (not shown) did not intersect any striations and the contact angle equals the intrinsic contact angle with the superhydrophobic surface, the second surface region 180. From the perpendicular point of view, the 3 phase contact line traverses the striations and contact angle is reduced to a magnitude between the superhydrophobic and hydrophobic contact angles (i.e. the contact angles at the second and first surface regions 180, 178). This represents a mitigation of contact angle by the interspersion of less hydrophobic regions.

The reduced contact angle is an average of undulating contact angles as the 3 phase contact line traverses the first and second surface regions 178, 180. To assess the meniscus reducing effects of the spacing and widths 182, 184 of first and second surface regions 178, 180 on meniscus magnitude in a culture well (not shown), a well plates with first and second surface regions 178, 180 having first widths of 1.0 and 2.0 mm respectively, were created. A volume of semisolid growth medium containing 1% methylcellulose was added to the well and the well was tilted to advance the liquid level up to contact the first and second surface regions 178, 180. After a 30 min equilibration period, meniscus magnitude was measured using the techniques described herein.

The results of these process, when compared to the meniscus reducing properties of a simple superhydrophobic coating, revealed that simple superhydrophobic coatings applied to the well's interior surface, while inverting the meniscus shape, produce similar optical interference for imaging as untreated surfaces. The striated first and second surface regions 178, 180 however, effectively reduced the meniscus magnitude, resulting in an observable undulating "dark area" where the meniscus transitioned periodically between convex and concave configurations. The maximum meniscus magnitude was reduced to 0.43 mm and 0.52 mm for striations with first surface regions widths 182 of 1.0 and 2.0 mm respectively. In addition, the relative optical interference compared to untreated wells was reduced by 98% for first surface regions widths 182 of 1.0 mm, and by 90% for first surface regions widths 182 of 2.0 mm.

Reducing the width of superhydrophobic regions may increase the frequency and reduce the size of the dark area and that the meniscus magnitude may be reduced by varying degrees with various combinations of first and second surface regions widths 182, 184.

TABLE 3

Effect of striations on contact angle with various aqueous liquids from two points of view (POV).

| Liquid | Spacing | POV | Contact angle |
|---|---|---|---|
| Water | 2 mm | parallel | 159 |
| Water | 2 mm | perpendicular | 121 |
| IMDM | 2 mm | parallel | 151 |
| IMDM | 2 mm | perpendicular | 130 |
| PBS/2% HSA | 2 mm | parallel | 123 |
| PBS/2% HSA | 2 mm | perpendicular | 117 |
| 1% methylcell | 2 mm | parallel | 132 |
| 1% methylcell | 2 mm | perpendicular | 116 |

In another example, striated patterns were generated on wall surfaces of 35 mm polystyrene dishes (not shown), by application of the WX2100 spray coating followed by the introduction of vertical hydrophobic regions using a blunt metal edge. In this manner, a striated surface with 1 mm superhydrophobic vertical bands interrupted by 0.5 mm and 1 mm wide first surface regions 178 was generated.

The hydrophobic or superhydrophobic coating material may be applied to the striated surface feature 132 using any suitable method, including: application or insertion of preformed materials (with or without adhesive); application of the material using a physical applicator followed by removal of excess material; application by immersion of the vessel into the coating material or a solution thereof, followed by drying; application of a melted material followed by cooling and solidification; dissolution of the coating material in a suitable solvent and application of this solution, followed by removal of the solvent through evaporation, aspiration, and/or washing; application of a material that cures upon exposure to air; and application of an agent following addition of the material that causes the material to cure.

It is understood that any type of meniscus reducing member 132 including a surface feature 134 may be integral with the sidewall 104 of the vessel 100 and comprise a portion of the interior surface 105. It is also understood that any type of meniscus reducing member 132 including a surface feature 134 may be provided on a separate insert member 146 that can be fixedly or removably received within a corresponding vessel 100.

What has been described above has been intended to be illustrative of the invention and non-limiting and it will be understood by persons skilled in the art that other variants and modifications may be made without departing from the scope of the invention as defined in the claims appended hereto.

We claim:

1. A meniscus reducing member comprising:
    a. a vessel, the vessel comprising a top, a closed bottom wall having a perimeter and defining a bottom plane and a sidewall extending around the perimeter of the bottom wall, the sidewall extending upwardly from a lower end adjacent the bottom wall to an upper end spaced between the lower end and the top of the vessel for retaining a given volume of liquid within the vessel, the sidewall comprising an engagement portion toward the upper end, the engagement portion comprising an exterior surface and an opposing interior surface that is substantially orthogonal to the bottom plane;
    b. a surface feature overlying at least a portion of the interior surface of the engagement portion to engage a free surface of the liquid within the vessel, the surface feature comprising a corrugated member to contact the liquid in the vessel and having a different shape than the exterior surface of the engagement portion, the corrugated member comprising a plurality of pairs of converging first and second surfaces, each pair of first and second surfaces intersecting to define an edge, the first surfaces, second surfaces and edges cooperate to reduce a width of a meniscus formed at an interface between the free surface of the liquid and the surface feature by physically altering a contact angle between the free surface of the liquid and the surface feature.

2. The meniscus reducing member of claim 1, wherein the first surface has a first slope angle and the second surface has a second slope angle, the first and second slope angles are each between 1 and 75 degrees.

3. The meniscus reducing member of claim 2, wherein the first and second slope angles are each between 5 and 50 degrees.

4. The meniscus reducing member of claim 2, wherein the first slope angle is different than the second slope angle.

5. The meniscus reducing member of claim 1, wherein the first surface has a first surface width and the second surface has a second surface width the first surface width is different than the second surface width.

6. The meniscus reducing member of claim 1, wherein the first surface has a first surface width and the second surface has a second surface width, the first surface width is equal to the second surface width.

7. The meniscus reducing member of claim 1, wherein adjacent edges are separated by an edge spacing distance, the edge spacing distance being set to reduce wetting of the first and second surfaces by the liquid due to a surface tension of the liquid.

8. The meniscus reducing member of claim 7, wherein the edge spacing distance is between 0.01 and 3 mm.

9. The meniscus reducing member of claim 1, wherein each edge has an edge height, each edge height is between 0.01 and 1.5 mm.

10. The meniscus reducing member of claim 1, wherein the surface feature has an axis that is perpendicular to a lower plane of the vessel.

11. The meniscus reducing member of claim 1, wherein the surface feature has an axis that is at an angle relative to a lower plane of the vessel, the angle being between 0 and 90 degrees.

12. The meniscus reducing member of claim 1, wherein the surface feature is integral with the sidewall of the vessel.

13. The meniscus reducing member of claim 1, wherein the surface feature extends continuously around an inner perimeter of the vessel.

14. A meniscus reducing member comprising:
a. a vessel, the vessel comprising a top portion, a closed bottom wall and a sidewall extending from the bottom wall for retaining a given volume of liquid within the vessel, the sidewall comprising an interior surface;
b. a surface feature overlying at least a portion of an interior surface of the vessel, the surface feature being disposed on a separate insert member configured to be received within the vessel and comprising a corrugated member to contact the liquid in the vessel, the corrugated member comprising a plurality of pairs of converging first and second surfaces, each pair of first and second surfaces intersecting to define an edge, the first surfaces, second surfaces and edges cooperate to reduce a width of a meniscus formed at an interface between the liquid and the surface feature by physically altering a contact angle between the liquid and the surface feature.

15. A meniscus reducing member comprising:
a. a vessel, the vessel comprising a top portion, a closed bottom wall and a sidewall extending from the bottom wall for retaining a given volume of liquid within the vessel, the sidewall comprising an interior surface;
b a surface feature overlying only a portion of a perimeter of the interior surface of the sidewall, the surface feature comprising a corrugated member to contact the liquid in the vessel, the corrugated member comprising a plurality of pairs of converging first and second surfaces, each pair of first and second surfaces intersecting to define an edge, the first surfaces, second surfaces and edges cooperate to reduce a width of a meniscus formed at an interface between the liquid and the surface feature by physically altering a contact angle between the liquid and the surface feature.

* * * * *

UNITED STATES PATENT AND TRADEMARK OFFICE
CERTIFICATE OF CORRECTION

| | |
|---|---|
| PATENT NO. | : 9,261,454 B2 |
| APPLICATION NO. | : 14/101892 |
| DATED | : February 16, 2016 |
| INVENTOR(S) | : Oliver Egeler et al. |

Page 1 of 1

It is certified that error appears in the above-identified patent and that said Letters Patent is hereby corrected as shown below:

In The Claims

In claim 3, line 62, the sentence that reads "first and second slope angles are each between 5 and 50 degrees." should read "first and second slope angles are each between 5 and 60 degrees."

In claim 5, line 1, the sentence that reads "has a second surface width the first surface width…" should read "has a second surface width, the first surface width…"

Signed and Sealed this
Seventeenth Day of May, 2016

Michelle K. Lee
*Director of the United States Patent and Trademark Office*